United States Patent
Lai

(10) Patent No.: US 10,660,855 B2
(45) Date of Patent: May 26, 2020

(54) PROCESS FOR PRODUCING A NANO-CBD LIPOSOME SYSTEM

(71) Applicant: Hai Nam Lai, Ho Chi Minh (VN)

(72) Inventor: Hai Nam Lai, Ho Chi Minh (VN)

( * ) Notice: Subject to any disclaimer, the term of this patent is extended or adjusted under 35 U.S.C. 154(b) by 0 days.

(21) Appl. No.: 16/537,597

(22) Filed: Aug. 11, 2019

(65) Prior Publication Data
US 2020/0000724 A1 Jan. 2, 2020

(30) Foreign Application Priority Data
Jan. 31, 2019 (VN) .............................. 1-2019-00610

(51) Int. Cl.
| | |
|---|---|
| *A61K 9/127* | (2006.01) |
| *A61K 47/24* | (2006.01) |
| *A61K 47/44* | (2017.01) |
| *A61K 31/05* | (2006.01) |

(52) U.S. Cl.
CPC ............ *A61K 9/1277* (2013.01); *A61K 31/05* (2013.01); *A61K 47/24* (2013.01); *A61K 47/44* (2013.01)

(58) Field of Classification Search
CPC ........ A61K 31/05; A61K 47/24; A61K 47/44; A61K 9/1277
See application file for complete search history.

(56) References Cited

U.S. PATENT DOCUMENTS 8,808,734 B2 * 8/2014 Winnicki ............... A61K 9/127
424/450

* cited by examiner

*Primary Examiner* — Nannette Holloman
(74) *Attorney, Agent, or Firm* — BN IP-Consulting LLC; Binh-An Nguyen

(57) ABSTRACT

The present invention relates to a process of producing a nano-CBD liposome system comprises: (i) preparing a dispersal phase by dissolving CBD in an ethanol solvent in a ratio between mass of CBD:volumn of ethanol solvent as 8:10 by a stirrer at a speed of 300 to 500 rpm and simultaneously heating to a temperature ranging from 40 to 60° C. within 4 to 8 hours; (ii) preparing a liposome carrier consisting of lecithin, olive oil in a ratio by mass of 1:3 mixed in a themostatic bath at a temperature from 40 to 60° C. to ensure that lecithin completely dissolves in oil, stirring homogeneously; (iii) adding the carrier to the dispersal phase in a ratio by mass of 40:60, continuing heating the dispersal phase to a temperature ranging from 40 to 60° C., stirring at a speed of 800 to 1000 rpm for 1 to 2 hours; (iv) cooling the resulting mixture to 25° C. and injecting one volumn of distilled water between 1 and 1.5 L by using hight-frequency nozzles at a frequency of 60 Hz, drop sizes ranging from 10 to 20 μm, injecting capacity of 10 ml/min, with the temperature of distilled water of 25° C., giving a liposome suspension-water solution; (v) homogenizing the mixture of liposome suspension-water solution by injecting through 30 Mpa high pressure homogenizers to obtain a nano-CBD liposome system which is a homogeneous, stable mixture ensured with the particle sizes <200 nm.

1 Claim, 1 Drawing Sheet

PROCESS FOR PRODUCING A NANO-CBD LIPOSOME SYSTEM

TECHNICAL FIELD

Figure 1:
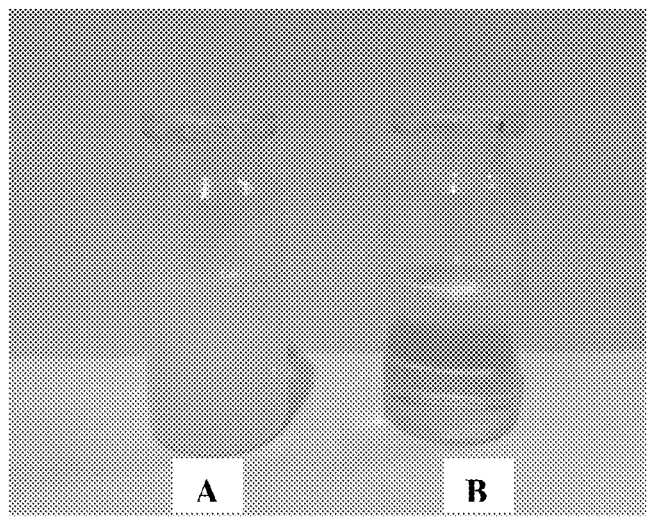
Figure 2:
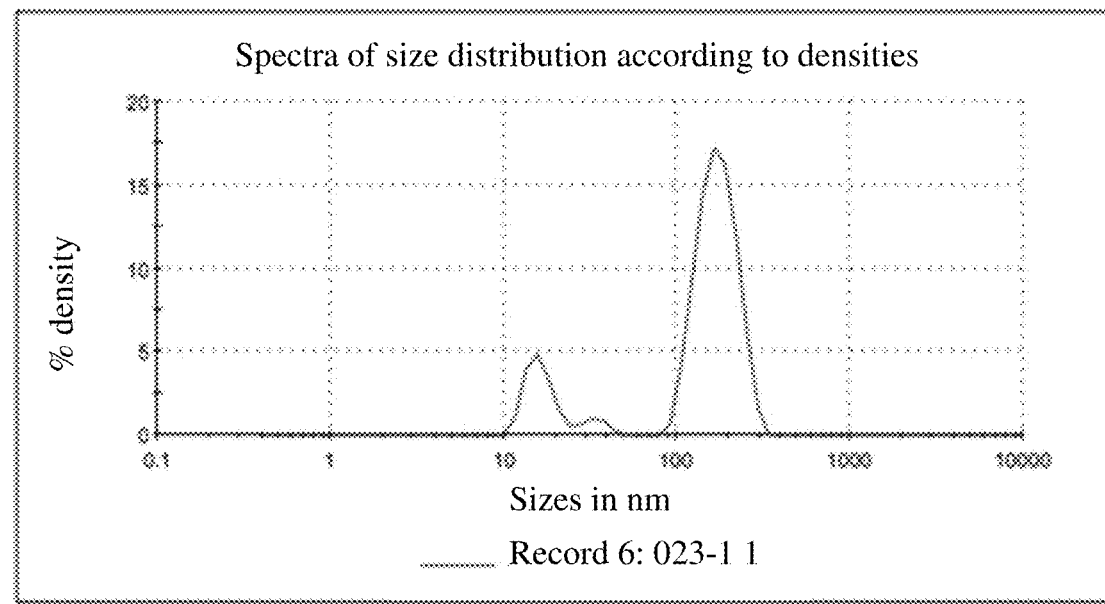

The present invention relates to a process for producing a nano-CBD liposome system.

BACKGROUND OF THE PRESENT INVENTION

Cannabidiol (CBD) is a cannabinoid which is a cyclohexene substituted by a methyl group at position 1, a 2,6-dihydroxy-4-pentylphenyl group at position 3 and a prop-1-en-2-yl group at position 4. It acts as a plant metabolite. Cannabidiol, a phytocannabinoid derived from *Cannabis* species, does not have psychophysiological activity, and is applied in pain-alleviation, anti-inflammation, anti-cancer and used in chemotherapies.

CBD is represented by chemical formula $C_{21}H_{30}O_2$, which has the molecular weight of 314.469 g/mol and the molecular structure as follows:

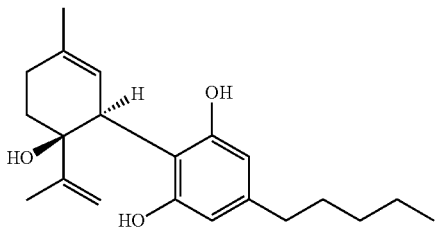 [SMILES: C=C(C)[C@]1(O)CCC(C)=C[C@H]1c1c(O)cc(CCCCC)cc1O]

When being used, cannabidiol (CBD) has actions against the proliferation, the angiogenesis and pro-apoptotic via various mechanisms, it may not relate to the signaling by cannabinoid receptors 1 (CB1), CB2 or vanilloid receptors and inhibits AKT/mTOR signals, therefore activates the autophagy—a process in which a cell "eats" the components of its own, which is a basically catabolic mechanism, related to the degration of unnecessary components or dysfunctioned components in the cell, via the actions of lysosomes and promotes the apoptosis—a process of programmed cell deaths. Additionally, CBD enhances the generation of reactive oxygen species (ROS), which helps to further enhance the apotosis. This agent also upregulates the expression of molecules adhered among cells 1 (ICAM-1) and issue inhibitors of matrix metalloproteinase-1 (TIMP1) and reduces the expression of DNA binding inhibitors 1 (ID-1). This inhibits the invasion of cancer and metastatic cells. CBD can also activate transiently potential vanilloids type 2 (TRPV2), which can increase the absorption of various cytotoxic agents in cancer cells. CBD has been demonstrated to have effects on pain-alleviation, anti-convolution, muscle stretching, anxiety-reduction, anti-oxidation, and anti-hysteria-epilepsy. These diverse effects may be due to the complex pharmacological mechanism of CBD. In addition to the constraint of CB1 and CB2 receptors of endocannabinoid systems, there is an evidence that CBD activates serotonines 5-HT1A and vanilloid receptors TRPV1-2, alpha-1 adrenergic antagonists and μ-opioid receptors, inhibits the synaptosomal absorption of noradrenalines, dopamines, serotonines and gaminobutyric acids and the cell absorption of anandamids, acts on Ca2 shops of mitochondrions, blocks low voltage-activated Ca2 channels (type T), stimulates the action of inhibitory glycine-receptors and inhibits the action of aliphatic hydrolases (FAAH).

CBD has high activity in the body but low bioavailability, according to the study by Mechoulam R et al., published on Journal of Clinical Pharmacology, the bioavailability when being used orally is only 13-19%, while being used nasally (inhalantly) is about 31%. It is fastly metabolised, and the half-life is within about 9 hours. CBD is well-absorbed after being administered orally, and has high activity in the body but low bioavailability. Thus, it is very necessary to improve the ability of absorption, increase the bioavailability of the agent. Applying nano technologies is a novel technological application for generating vehicle systems and increasing the bioavailability of the agent. In particular, the application of a liposome system, which is a new system having the structure composed of sphere subunits and very small dimensions (nano-sized), containing nutrient active agents in its core and being surrounded outside by one or more dependent phospholipid membranes, is capable of containing, protecting, transporting and releasing active agents to desired sites of the body exactly and with proper dosages. CBD packaged in nano-vehicle systems helps transport an agent to targets in a selectively, effectively and drug-saving way. In our country, nano technologies in biomedical fields remain new, not yet have many applications but have attracted so much interest to study. The most common existing studies are the applications of nanocurumin and drug transporting systems to target cells, there have not been studies to manufacture nano-CBDs. Using the liposome system generating nanoparticles to carry and release drugs is a new strategy for treating diseases, particularly epilepsy and cancers in the future.

GART et al. in Patent Publication No. WO 2018/061007 A1 provided vehicle systems of cannabinoids in the form of microemulsions.

Robert WINNICKI et al. in Patent Publication No. WO2013009928A1 provided cannabinoid formulae. One kind of solution micelle suspensions of one or more cannabinoid analogues creates particles with dimensions of 50 to 1000 nm, another kind is a liposome formula of one or more cannabinoid analogues with particle sizes of 200 to 400 nm.

By micro- and micelle-emulsifying methods, the mentioned-above processes produce ununiform micelles, particularly produce nano-CBDs with dimensions greater than 200 nm according to liposome formula, thus the water-soluble effect and utility effect are still not high.

Therefore, there is a demand of a process for producing a nano-CBD liposome system consisting of micelles of the liposome system which have dimensions less than 200 nm, uniformity, better water-solubility and retain the structure, activity of CBD in nanoprocessing.

SUMMARY OF THE PRESENT INVENTION

An object of the present invention is to provide a process for producing a nano-CBD liposome system that aims at overcoming disadvantages of the known mentioned-above processes to produce particles having dimensions smaller than 200 nm, uniformity, ability to dissolve in water while activity and structure is retained to help increase utility effects of CBD active agents, in particular, increase the ability of absorption and increase the bioavailability.

To achieve the above object, the process for producing a nano-CBD liposome system of the present invention includes:

(i) Step 1: preparing a dispersal phase by dissolving CBD in an ethanol solvent in a ratio between mass of CBD: volumn of ethanol solvent as 8:10 by a stirrer at a speed of 300 to 500 rpm with heating to a temperature ranging from 40 to 60° C. within 4 to 8 hours;

(ii) Step 2: preparing a liposome carrier comprising lecithin, olive oil in a ratio by mass of 1:3 mixed in a themostatic bath at a temperature from 40 to 60° C. to ensure that lecithin completely dissolves in the oil, stirring homogeneously.

(iii) Step 3: adding the carrier to the dispersal phase in a ratio by mass of 40:60, continuing heating the dispersal phase to a temperature ranging from 40 to 60° C., stirring at a speed of 800 to 1000 rpm, for 1 to 2 hours.

(iv) Step 4: cooling the resulting mixture to 25° C. and injecting one volumn of distilled water ranging from 1 to 1.5 L by using hight-frequency nozzles at a frequency of 60 Hz, having drop sizes of 10 to 20 μm, injecting capacity of 10 ml/min, with the temperature of distilled water at 25° C., obtain a liposome suspension-water solution;

(v) Step 5: homogenizing the mixture of liposome suspension-water solution by injecting through 30 Mpa high pressure homogenizers to obtain a nano-CBD liposome system which is a homogeneous, stable mixture ensured with the particle sizes <200 nm.

BRIEF DESCRIPTION OF DRAWINGS

FIG. 1 shows a picture comparing the water-dispersing ability between a known CBD and the nano-CBD obtained by the process of the present invention.

FIG. 2 shows a picture of spectra measuring by TEM the particle sizes of nano-CBD liposomes obtained by the process of the invention.

DETAILED DESCRIPTION OF THE INVENTION

The process for producing a nano-CBD liposome system of the present invention is performed as follows:

(i) First step: preparing a dispersal phase by dissolving CBD in an ethanol solvent in a ratio between mass of CBD:volumn of ethanol solvent as 8:10 by a stirrer at a speed of 300 to 500 rpm and simultaneously heating to a temperature ranging from 40 to 60° C. within 4 to 8 hours. The inventors used ethanol as a solvent which is capable of dissolving CBD well, helps create a better dispersal phase and facilitates this dispersal phase with better combining with PEG carriers. The use of hydroxyl (OH—)-based ethanol solvent provides a linkage with water, thus has effects on stabilizing the structure of the oil-in-water liposome system. By experiments, the inventors determined that, in 8:10 ratio of CBD:ethanol (mass:volumn), CBD achieved the highest solubility and avoided the redundance of ethanol solvent, which is a wastage. The use of stirring and heating provides CBD dispersing better, when the inventors performed experiments under various stirring conditions and temperatures, it was shown that at a speed of 300-500 rpm with heating to a temperature ranging from 40 to 60° C., the dispersal phase of CBD was better and the combination with PEG carriers was better.

(ii) Second step: preparing a liposome carrier consisting of lecithin, olive oil in a ratio by mass of 1:3 mixed in a themostatic bath at a temperature ranging from 40 to 60° C. to ensure that lecithin completely dissolves in oil, stirring homogeneously.

When being used, CBD is often damaged in the digestive tract, a portion is absorped into the blood, most of the rest is eliminated. Hence, it is necessary to have a process for producing micelles which contain CBD active agents, have small sizes with bio-coatings, stable structures, inadherence and high solubility. Because the nano-CBD liposome system of the present invention is employed in cosmetic and pharmaceutical industries, the agents selected to use must have high safety, non-toxicity and less side effects.

Surfactants are used to confer the system the stability and homogeneity, prevent the agents in this system from flocculating and adhering, herein the inventors used lecithin (phospholipids). In this procedure, we used soy lecithin, which is safe for users and has reasonable costs. The molecular formula of lecithin, according to the publication of Willstatter in 1918, is composed of glyxerophosphoric acid, fatty acid and choline, these 3 components can combine together in many ways to provide many kinds of lecithins. Two fatty acid molecules attract each other thereby they are in the same orientation, the ends of fatty acid containing hydrophobic moieties form a hydrophobic portion of lecithin. The bond of $C_2$-$C_3$ in the glycerine moiety may be twisted by 180° that makes the polar P group be upstream with the fatty acid chain, forms a hydrophylic end of lecithin. Because of the especial structure, lecithin molecules are amphiphilic (oleophilic). It is an advantage to apply lecithin to form the liposome system. The liposome system can trap water-soluble active agents (hydrophylic) in a capacity containing water therein and water-insoluble active agents (hydrophobic) in bilayer membranes thereof. The second character makes it be possible to use liposome to form nano-CBD particles that are compatible with water. After a plural of experiments, the inventors selected lecithin, olive oil with the ratio by mass of 1:3 to achieve the stablest system.

(iii) Third step: adding the carrier to the dispersal phase in a ratio by mass of 40:60, continuing heating the dispersal phase to a temperature from 40 to 60° C., stirring at a speed of 800 to 1000 rpm for 1 to 2 hours.

(iv) Fourth step: the resulting mixture is cooled to 25° C. and injected by using ultrasonic atomizer nozzles at a frequency of 60 Hz (drop size of 20 μm, 10 ml/minute), into 1-2 L of distilled water (the temperature of distilled water is 25° C.). The liposome suspension-water solution is concentrated by rotary evaporator at a pressure from 20 to 30 mm Hg and a temperature under 55° C.

Nanoparticles tend to aggregate, it is necessary to provide enough energy to detach linkage forces to disperse nanoparticles. Using ultrasonic atomizer nozzles is a effective means in dispersing nanoparticles and reducing nanoparticle sizes, forming particles with smaller and more uniform sizes. Dispersing and disrupting the aggregation of nanoparticles are the results of the cavitation due to ultrasonic waves. When ultrasonic waves spread into the solvent, it will continue forming alternate cycles between high and low pressures, this affects on linkage forces of nanoparticles. At the same time, when series of foams crumble, this will create a very high pressure affecting on nanoparticle beads that makes them be easily detached together.

(v) Fifth step: homogenizing the mixture by injecting through high pressure homogenizers 30 Mpa (300 bar). The homogenization of the suspension is to reduce particle sizes within the dispersal phase and distribute them evenly in the continuous phase to restrict phase separations under gravity actions, ensure the uniformity, stability of solutions, and increase the durability of products.

Using ultrasonic waves helps affect nanoparticles, makes them not adhere together, however, a disadvantage of this method is that ultrasonic ends are made of metals, when accelerating ultrasonic waves with high intensities they can make products be titanium-contaminated. To ensure the safety of products, the inventor group carried out experiments and chose the frequency 60 Hz to separate nanoparticles while still ensure the product safety. However, at this frequency, nano-products do not maintain the particle stability for a long time, the expiration date of products is short. To increase the durability and stability, the inventor group injected the obtained solutions through high pressure homogenizers 300 bar to ensure the uniformity, the stability of the solution, increase the durability of the products.

The liposome system obtained by the process of the invention has pH of 7-7.5. With these pH values, micelles exist stably because the bond between CBD and carrying material is kept in the dispersing process in this neutral environment, while the nanoliposome system has pH <7, then this bond weakens resulting the damage of nano-CBD particles in the digestive tract.

The nano-CBD liposome system obtained by the process of the present invention having HLB of 13 to 18 is a hydrophylic liposome system. The liposome system has micelles which contain hydrophylic CBDs, are inadherent with particle sizes ranging stably from 10 to 200 nm, hence it can easily penetrate cell membranes to develop the effectiveness and increase the solubility of CBDs in water, thus enhance the bioavailability of agents.

EXAMPLES

Example: Production of 1000 ml of Nano-CBD Liposome System

A dispersal phase was prepared by dissolving 80 g of CBD in 100 g of ethanol solvent via a magnetic heating stirrer KIA—Germany C-MAG HS4/7/10 at a speed of 400 rpm and simultaneously heated to 50° C. for 6 hours to give 180 g of a dispersal phase.

Preparing a liposome carrier consisting of 30 g of lecithin and 90 g of olive oil mixed in a themostatic bath Labtech LWB-106D, 1200 W, at 50° C. to ensure that lecithin completely dissolved in olive oil, stirring homogeneously for 30 minutes to give 120 g of a carrier solution.

120 g of a carrier was added to 180 g of the dispersal phase, the dispersal phase continued to be heating to 50° C., stirred at a speed of about 9000 rpm for 2 hours.

The resulting mixture was cooled to 25° C. and injected by using ultrasonic atomizer nozzles (Ultrasonic Atomizer Nozzle Machine, 100 W, 30 Khz) at a frequency of 60 Hz (the ultrasonic atomizer nozzles have drop sizes ranging from 10 to 20 μm, injecting capacity of 10 ml/min) to 1 Litter of distilled water (at 25° C.), giving a liposome suspension-water solution. The liposome suspension-water solution was concentrated by rotary evaporator at a pressure of 20 to 30 mm Hg and a temperature under 55° C. until 1000 ml of suspension solution left.

The mixture was homogenized by injecting through 30 Mpa high pressure homogenizers. Obtaining 1000 ml of nano-CBD liposome system which is a homogeneous, stable mixture ensured with the particle sizes <200 nm.

By UV-vis spectrophotometry methods, the inventors found that positions of peaks of the material CBD and the nano-CBD liposome system fitted completely. This showed that the liposome system obtained by the process of the present invention retained the structure, activity of CBDs in nanoprocessing. UV-vis spectrophotometry methods were utilized to quantify the concentrations of CBDs in the liposome system. The results showed that the concentrations of CBDs in the nano-CBD liposome system were in the range of 8 to 10%.

Measuring sizes of nano-CBD particles by a scanning electron microscopy TEM (Transmission Electron Microscopy) shown in FIG. 2 demonstrated that particle sizes fluctuating from 10 to 200 nm accounted for 81.3% in solution.

Particle sizes measured by DLS: particles suspending in a fluid continued undergoing random motions, and the particle sizes affected directly on their speeds. Small particles moved faster than bigger ones. In DLS, lights went through samples, and scattering lights were detected and recorded in a certain angle.

Zeta potential or kinetic potential: the potential between a dispersal phase and a dispersing media.

| Sizes (nm, according to TEM) | Sizes (nm, according to DLS) | Zeta potential (mV) | Stability (months) | Water-solubility |
|---|---|---|---|---|
| 10-200 | 10-200 | −40 | >12 | Well solubilized in water, after solubilizing in water, the system stabilized >30 days |

The above results showed that, the liposome system had micelles with dimensions smaller than 200 nm, high stability (>12 months), well-water solubility and after dissolved in water, the system stabilized >30 days.

With the reference to FIG. 1, it shows a picture comparing the water-dispersing ability between a 99% known CBD and the nano-CBD obtained by the process of the present invention, in which bottle A showed the known 99% water-dispersed CBD, bottle B showed the water-dispersed nano-CBD obtained by the process of the invention. FIG. 1 showed that the known 99% CBD was insoluble in water, formed water-suspending particles, a cloudy solution which encrusted at the bottom of bottle (A) over time; the nano-CBD obtained by the process of the present invention completely dispersed in water generated a transparent, homogeneous solution (B).

With the reference to FIG. 2 showing the results of a picture of spectra measuring by TEM the sizes of nano-CBD particles obtained by the process the present invention, it was found that the average particle size was 81.65 nm, at density of 81.3%, with spectrum peak 1 having the particle diameter of 174.3 nm, the width of 44.03 nm. Particles had the uniformity of sizes fluctuating from 10 to 200 nm (FIG. 2), appeared spectrum peak 2 having the particle diameter of 16.2 nm, the width of 2.966 nm but accounted for only 15.3%, spectrum peak 3 having the particle diameter of 32.9 nm, the width of 5.776 nm but accounted for only 3.4%.

Table below showed measurement data:

| | | Diameter (nm) | % density | Width (nm) |
|---|---|---|---|---|
| Average particle size (d.nm): 81.65 | Spectrum peak 1 | 174.3 | 81.3 | 44.03 |
| PdI: 0.412 | Spectrum peak 2 | 16.2 | 15.3 | 2.966 |

-continued

| | Diameter (nm) | % density | Width (nm) |
|---|---|---|---|
| Blocking ability: 0.953 | Spectrum peak 3 | | |
| Result of evaluation: good | | 32.9 | 3.4 | 5.776 |

Advantageous Effects of Invention

The process for producing a nano-CBD liposome system in accordance of the present invention succeeds in manufacturing a liposome system having nano-CBD micelles with dimensions smaller than 200 nm, uniformity and well-water solubility while retaining the structure and activity of CBDs in nanoprocessing.

Agents used in the process for producing nano-CBDs, which disperse well in water, have high safety, non-toxicity and less side effects, thus the nano-CBD liposome system obtained by the process of the present invention has high safety when being used.

The present process is simple, easy to carry out and suitable with current actual conditions of our country.

The invention claimed is:

1. A process for producing a nano-CBD liposome system comprises:

(i) preparing a dispersal phase by dissolving CBD in an ethanol solvent in a ratio between mass of CBD: volumn of ethanol solvent as 8:10 with a stirrer at a speed of 300 to 500 rpm with heating to a temperature from 40 to 60° C. within 4 to 8 hours;

(ii) preparing a liposome carrier consisting of lecithin, olive oil in a ratio by mass of 1:3 mixed in a themostatic bath at a temperature ranging from 40 to 60° C. to ensure that lecithin completely dissolves in oil, stirring homogeneously;

(iii) adding the carrier to the said dispersal phase in a ratio by mass of 40:60, continuing heating the dispersal phase to a temperature of 40 to 60° C., stirring at a speed of 800 to 1000 rpm for 1 to 2 hours;

(iv) cooling the resulting mixture to 25° C. and injecting one volumn of distilled water of 1 to 1.5 L by using hight-frequency nozzles at a frequency of 60 Hz, having drop sizes ranging from 10 to 20 µm, injecting capacity of 10 ml/min, with the temperature of distilled water of 25° C., achieved a liposome suspension-water solution;

(v) homogenizing the mixture of liposome suspension-water solution by injecting through 30 Mpa high pressure homogenizers to obtain a nano-CBD liposome system which is a homogeneous, stable mixture ensured with the particle sizes <200 nm.

* * * * *